United States Patent
Ohta et al.

(10) Patent No.: US 6,641,804 B1
(45) Date of Patent: Nov. 4, 2003

(54) HAIR TREATMENT AND METHOD OF TREATING HAIR USING COMPOUNDED RESIN CONTAINING URETHANE RESIN

(75) Inventors: Atsushi Ohta, Kyoto (JP); Hiroshi Itayama, Kyoto (JP); Masaya Tomioka, Kyoto (JP)

(73) Assignee: Sanyo Chemical Industries, Ltd., Kyoto (JP)

( * ) Notice: Subject to any disclaimer, the term of this patent is extended or adjusted under 35 U.S.C. 154(b) by 0 days.

(21) Appl. No.: 09/622,571

(22) PCT Filed: Jan. 26, 1999

(86) PCT No.: PCT/JP99/00296

§ 371 (c)(1),
(2), (4) Date: Aug. 18, 2000

(87) PCT Pub. No.: WO99/43289

PCT Pub. Date: Sep. 2, 1999

(30) Foreign Application Priority Data

Feb. 24, 1998 (JP) .............................................. 10/60587
Jan. 5, 1999 (JP) ................................................ 11/256
Jan. 21, 1999 (JP) ............................................. 11/13283

(51) Int. Cl.[7] .................................................. A61K 7/11
(52) U.S. Cl. ................. 424/70.12; 424/70.1; 424/70.11; 424/70.15; 424/70.16; 424/70.17; 424/47
(58) Field of Search ............................ 424/70.1, 70.11, 424/70.12, 70.17, 47, 70.15, 70.16; 510/119; 8/405

(56) References Cited

U.S. PATENT DOCUMENTS

| | | |
|---|---|---|
| 2,531,468 A | 11/1950 | Reynolds et al. ........... 260/79.3 |
| 2,604,461 A | 7/1952 | Roth ........................ 260/79.3 |
| 2,837,500 A | 6/1958 | Andres et al. ............. 260/79.3 |
| 3,008,918 A | 11/1961 | Stanton et al. ............. 260/45.5 |
| 3,257,281 A | 6/1966 | Maeder ....................... 167/87.1 |
| 3,320,212 A | 5/1967 | Shen et al. .................... 260/49 |
| 3,576,760 A | 4/1971 | Gould et al. ................. 252/403 |
| 3,577,518 A | 5/1971 | Shepherd et al. ............. 424/47 |
| 3,644,303 A | 2/1972 | Berger et al. ............... 260/79.3 |
| 3,671,502 A | 6/1972 | Samour et al. ............ 260/79.3 |
| 3,706,717 A | 12/1972 | Siegele ....................... 260/78.5 |
| 3,937,802 A | 2/1976 | Fujimoto et al. ............. 424/47 |
| 5,626,840 A | 5/1997 | Thomaides et al. ...... 424/70.11 |
| 6,335,003 B1 * | 1/2002 | Kim et al. |

FOREIGN PATENT DOCUMENTS

| | | |
|---|---|---|
| CA | 2148805 | 10/2000 |
| JP | 61-57803 B | 8/1980 |
| JP | 5-310538 A | 11/1993 |
| JP | 8-26938 A | 1/1996 |
| JP | 8-504454 A | 5/1996 |
| JP | 8-291032 A | 11/1996 |
| JP | 10-203937 A | 8/1998 |
| JP | 10-259115 | * 9/1998 |

* cited by examiner

Primary Examiner—Jyothsna Venkat
(74) Attorney, Agent, or Firm—Finnegan, Henderson, Farabow, Garrett & Dunner, L.L.P.

(57) ABSTRACT

A hair treating agent comprising: a resin and a diluent, the resin (T) providing a resin film having a tan δ of 0.3 or less and having a 100% modulus of 8 to 40 kgf/cm$^2$ as measured after being conditioned at 30° C. and 80%RH, and being at least one resin selected from the group consisting of vinyl resins, polyester resins, polyamide resins, silicone resins, cationic urethane resins, ampholytic urethane resins and nonionic urethane resins. The treating agent is excellent in setting property and washing removability when utilized as a hair fixative, and excellent in conditioning effect when utilized as a shampoo, rinse and hair dye.

5 Claims, 1 Drawing Sheet

100% R.H. (relative humidity) and being at least one resin selected from the

HAIR TREATMENT AND METHOD OF TREATING HAIR USING COMPOUNDED RESIN CONTAINING URETHANE RESIN

This application is a 371 of PCT/JP99/00296 filed Jan. 26, 1999.

TECHNICAL FIELD

The present invention relates to a hair treating agent and a hair treating method. More particularly, it relates to a hair treating agent usable as a hair fixative excellent in setting property and washing removability and as a shampoo, rinse and hair dye excellent in conditioning effect, and a hair treating method using this hair treating agent.

BACKGROUND ART

Conventionally, an aqueous or alcoholic resin solution of a vinyl resin (Japanese Patent Publication (JP-B) No. 61-57803) an anionic urethane resin (Japanese Patent Lay-Open (JP-A) No. 6-321741) or the like has been used as a hair treating agent for setting hair.

However, the conventional hair treating agents manifest high hygroscopic property of a resin film, and therefore has a defect that the ability of setting hair becomes weaker under high humidity. Further, when a resin is hydrophobicized or the strength of a resin film is increased to improve the setting ability, the resin can not be removed completely in hair washing, problematically.

SUMMARY OF THE INVENTION

Accordingly, one object of the present invention is to provide a hair treating agent suitable as a hair fixative, capable of retaining high setting property even under high humidity and being removed easily in hair washing. Another object of the present invention is to provide a hair treating agent having excellent conditioning effect also suitable as a shampoo, rinse, hair dye and the like. Still another object of the present invention is to provide a method for treating hair using these hair treating agents.

According to the present invention, provided is a hair treating agent comprising a resin (T) and a diluent, the resin (T) providing a resin film having a tan $\delta$ of 0.3 or less and having a 100% modulus of 8 to 40 kgf/cm$^2$ as measured after being conditioned at 30° C. and 80%R.H. (relative humidity) and being at least one resin selected from the group consisting of vinyl resins, polyester resins, polyamide resins, silicone resins, cationic urethane resins, ampholytic urethane resins and nonionic urethane resins. In another aspect, the present invention provides a hair treating method for treating hair using such a hair treating agent.

Herein, tan $\delta$ represents the ratio of the viscosity to the elasticity of a resin, and higher this ratio, the higher the viscosity of a resin. 100% modulus represents a stress when a resin film is elongated 2-fold, and the higher this value, the more easily a resin is elongated.

DETAILED DESCRIPTION OF THE PREFERRED EMBODIMENTS

Specific Examples of Vinyl Resin

Figure 1:
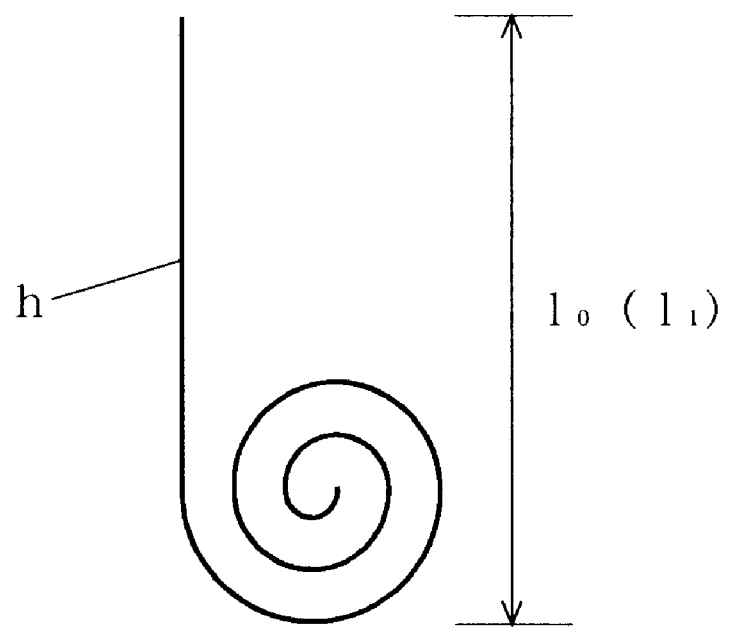
FIG. 1 is a view explaining the length of curl measured in testing the setting property of the hair treating agent of the present invention.

In the present invention, suitable vinyl resins, the composition of which is not particularly restricted, include ones obtainable by polymerization of a vinyl monomer. As the vinyl monomer, there may be specifically listed monomers as (a) to (e) described below, and one or more of them can be used.

(a) Anionic Vinyl Monomers

1. Anionic Vinyl Monomers Containing a Carboxyl Group or Their Salts

Unsaturated monocarboxylic acids [(meth)acrylic acids, crotonic acid, cinnamic acid and the like], unsaturated dicarboxylic acids (maleic acid, itaconic acid, fumaric acid and the like) and their salts (alkali metal salts, ammonium salts, amine salts and the like).

2. Anionic Vinyl Monomers Containing a Sulfonic Group or Their Salts

Vinylsulfonic acid, (meth)allylsulfonic acids, styrenesulfonic acids, 2-hydroxy-3-allyloxy-1-propanesulfonic acid, isoprenesulfonic acid and 2-acrylamido-2-methylpropanesulfonic acid, and their salts (alkali metal salts, ammonium salts, amine salts and the like).

(b) Cationic Vinyl Monomers

1. Cationic Acrylic Vinyl Monomers (1) Quaternary Nitrogen-containing (Meth)acrylates 2-(meth)acryloyloxyalkyl (2 to 5 carbon atoms)trialkyl(1 to 4 carbon atoms)ammonium salts and the like; for example, 2-(meth)acryloyloxyethyltrimethylammonium chlorides, 2-(meth)acryloyloxyethyltrimethylammonium methosulfates and the like.

(2) Tertiary Nitrogen-containing (Meth)acrylates and Their Salts

Dialkyl(1 to 4 carbon atoms)aminoalkyl(2 to 5 carbon atoms)(meth)acrylates and their salts; for example, dimethylaminoethyl(meth)acrylates and their sulfates, dimethylaminoethyl(meth)acrylates and hydrochloride thereof, diethylaminoethyl(meth)acrylates and hydrochloride thereof, dimethylaminoethyl(meth)acrylates and organic acid salt (acetate, lactate or the like) thereof and the like.

(3) Quaternary nitrogen-containing (Meth)acrylamides (Meth)acrylamidoalkyl(2 to 5 carbon atoms)trialkyl(1 to 4 carbon atoms)ammonium salts; for example, 2-(meth) acrylamidoethyltrimethylammonium chlorides, 2-(meth) acrylamidoethyltriethylammonium sulfates and the like.

(4) Tertiary Nitrogen-containing (Meth)acrylamides and Their Salts

Dialkyl(1 to 4 carbon atoms)aminoalkyl(2 to 5 carbon atoms)(meth)acrylamides and their salts; for example, 2-dimethylaminoethyl(meth)acrylamides and hydrochlorides thereof, N-methyl(meth)acrylamides and hydrochlorides thereof, N,N-dimethylaminopropyl(meth)acrylamides and hydrochlorides thereof and the like.

(5) Quaternary Phosphonium Salt-containing (Meth) acrylates 2-(meth)acryloyloxyalkyl(2 to 5 carbon atoms)trialkyl(1 to 4 carbon atoms)phosphonium salts and the like; for example, 2-(meth)acryloyloxyethyltrimethylphosphonium chlorides, 2-(meth)acryloyloxyethyltributylphosphoniumammonium chlorides and the like.

2. Vinylbenzyl Cationic Monomers

Vinylbenzyltrialkyl(1 to 4 carbon atoms)ammonium salts (vinylbenzyltrimethylammonium chloride and the like) and the like.

3. Dialkyldiallyl Cationic Vinyl Monomers

Dialkyl(1 to 4-carbon atoms)diallylammonium salts (dimethyldiallylammonium chloride and the like) and the like.

4. Other Cationic Vinyl Monomers

Vinylimidazoline and the like.

(c) Ampholytic Vinyl Monomers

N-(meth)acryloyloxyalkyl(1 to 10 carbon atoms)- or N-(meth)acryloylaminoalkyl(1 to 10 carbon atoms)- or N,N,-dialkyl(1 to 5 carbon atoms)ammonium-N-alkyl(1 to 5 carbon atoms)carboxylates; for example, N-(meth)acryloyloxyethyl-N,N-dimethylammonium N-methylcarboxylates, N-(meth)acryloylaminopropyl N,N-dimethylammonium N-methylcarboxylates, N-(meth) acryloyloxyethyl N,N-dimethylammonium propylsulfates and the-like.

(d) Nonionic Vinyl Monomers 1. (Meth)acrylic Esters (Meth)acrylates containing a hydrocarbyl group having 1 to 22 carbon atoms, such as methyl (meth)acrylates, ethyl (meth)acrylates, butyl (meth)acrylates, hexyl (meth) acrylates, octyl (meth)acrylates, lauryl (meth)acrylates, stearyl (meth)acrylates, behenyl (meth)acrylates, oleyl (meth)acrylates and 2-ethylhexyl (meth)acrylates.

2. Hydroxyl Group-containing Vinyl Monomers

Hydroxyalkyl(2 to 5 carbon-atoms)(meth)acrylates [such as hydroxyethyl(meth)acrylates] and the like.

3. Polyoxyalkylene Group-containing Vinyl Monomers

Polyoxyethylene(polymerization degree=1 to 100)(meth) acrylates, polyoxypropylene(polymerization degree=1 to 100) (meth)acrylates, (meth)acrylates of alkyleneoxide(2 to 4 carbon atoms)adducts(polymerization degree=1 to 100) of higher alcohol having 6 to 22 carbon atoms [Polyoxyethylene(polymerization degree=1 to 100)stearyl (meth)acrylates] and the like.

4. Other Nonionic Vinyl Monomers

Vinyl acetate, acrylonitrile, styrene, chlorostyrenes, 4-vinylstyrene, N-vinylpyrrolidone, butadiene and the like.

(e) Cross-linking Component

Vinyl monomers having 2 or 3 or more unsaturated bonds in one molecule [Ethylene glycol di(meth)acrylates, trimethylolpropane triacrylate, polyethylene glycol [polymerization degree=1 to 100] di(meth)acrylates and the like] and the like.

Among resins of these monomers, preferred are vinyl resins containing a cationic vinyl monomer as a part of the composition and vinyl resins containing an ampholytic vinyl monomer as a part of the composition.

The vinyl resin, constituent component of the treating agent of the present invention can be obtained by a conventional production method, for example, by polymerizing a monomer as above in the presence of a polymerization initiator. A polymerization method for producing the vinyl resin of the invention is not particularly restricted, and the vinyl monomer can be polymerized by any of known methods such as solution polymerization, emulsion polymerization, suspension polymerization, bulk polymerization and the like. The emulsion polymerization is preferred.

Solvents usable in the polymerization are not particularly restricted, and include, for example, alcoholic solvents such as methanol, ethanol and isopropyl alcohol; ketone solvents such as dimethylketone, methylethylketone and diethylketone; ester solvents such as ethyl acetate and butyl acetate; ether solvents such as methylcellosolve, ethylcellosolve and butylcellosolve; water, and the like. Preferable are water and alcoholic solvents.

Polymerization catalysts, not particularly restricted, include, for example, azo polymerization catalysts such as azobisisobutyronitrile, azobisvaleronitrile and azobiscyanovaleric acid; and peroxide catalysts such as benzoyl peroxide and di-t-butyl peroxide. The temperature in the polymerization is usually from 50 to 220° C., preferably from 70 to 120° C. The polymerization is preferably conducted within an atmosphere of an inert gas such as nitrogen.

Specific Examples of Polyepser Resin

Suitable polyester resins, the composition of which is not particularly restricted, include polycondensates of a polycarboxylic acid having 2 or more carboxyl groups or anhydride thereof with a polyol having 2 or more hydroxyl groups, polycondensates of a compound having a carboxyl group and a hydroxyl group in the same molecule or an internal cyclic ester thereof, and the like, As the polycarboxylic acid having 2 or more carboxyl groups or anhydride thereof, there may be listed aromatic polycarboxylilc acids (anhydrides), aliphatic saturated polycarboxylic acids (anhydrides), aliphatic unsaturated carboxylic acids (anhydrides) and the like.

Aromatic polycarboxylic acids (anhydrides) include polycarboxylic acids having 2 to 6 functional groups and 8 to 30 carbon atoms, for example, phthalic anhydride, isophthalic acid, terephthalic acid, tetrabromophthalic anhydride, tetrachlorophthalic anhydride, trimellitic anhydride, pyromellitic anhydride and the like.

Aliphatic saturated polycarboxylic acids (anhydrides) include polycarboxylic acids having 2 to 6 functional groups and 3 to 30 carbon atoms, for example, succinic anhydride, adipic acid, azelaicacid, sebacicacid, hexahydrophthalic anhydride and the like.

Illustrative of aliphatic unsaturated polycarboxylic acids (anhydrides) are polycarboxylic acids having 2 to 6 functional groups and 4 to 30 carbon atoms, for example, tetrahydrophthalic anhydride, HET anhydride, hymic anhydride, maleic anhydride, fumaric anhydride, itaconic anhydride, methylcyclohexenetricarboxylic anhydride and the like.

Of them, aliphatic polycarboxylic acids are preferable. The polycarboxylic acids can be used alone or in admixture of two or more.

As the polyol having 2 to more hydroxyl groups, low molecular weight polyols, high molecular weight polyols and the like can be listed.

As low molecular weight polyols, there may be mentioned low molecular weight dihydric polyols, low molecular weight trihydric polyols, low molecular weight tetrahydric or more polyols, and the like.

Low molecular weight dihydric polyols are inclusive of diols of a hydrocarbon group having 2 to 30 carbon atoms which may contain ether linkage or linkages, for example, ethylene glycol, propylene glycol, tetramethylene glycol, 1,3-butylene glycol, 1,6-butylene glycol, diethylene glycol, neopentyl glycol, triethylene glycol, hydrogenated bisphenol A, bisphenol dihydroxypropyl ether; diols having 2 to 30 carbon atoms containing a tertiary amino group, for example, N-methyldiethanolamine, N-ethyldiethanolamine, N-methyldibutanol and the like. Low molecular weight trihydric polyols include triols of a hydrocarbon group having 3 to 30 carbon atoms, for example, glycerine, trimethylolethane, trimethylolpropane and the like. As low molecular weight tetra-hydric or more polyols, there may be listed polyols of a hydrocarbon group having 4 to 30 carbon atoms, for example, pentaerythritol, dipentaerythritol, sorbitol, diglycerine, polyglycerine and the like. High molecular weight polyols include alkylene oxide (2 to 4 carbon atoms) adducts (polymerization degree=1 to 100) of a low molecular weight polyol as mentioned above, and have a functionality of from 2 to 4 or more and a molecular weight of from 1000 to 20000. These polyols may be used alone or in admixture of two or more.

Exemplary of the compound having a carboxyl group and a hydroxyl group in the same molecule or the internal cyclic ester thereof are lactones having 4 to 10 carbon atoms such as ε-caprolactone, γ-butyrolactone, γ-valerolactone and the like.

The polyester resin, constituent component of the treating agent of the present invention can be obtained by a conventional production method, for example, by polycondensing a polycarboxylic acid and a polyol as mentioned above. The polyester resin may also be obtained by polycondensation of a lower mono-hydric alcohol ester of a polycarboxylic acid, for example, a de-methanol reaction of a polymethyl ester thereof with a polyol. Further, the polyester resin can also be obtained by ring-opening polymerization of a cyclic ester. The polycondensation temperature is usually from 100 to 300° C., preferably from 130 to 220° C. The polymerization is preferably conducted within an atmosphere of an inert gas such as nitrogen.

The equivalent ratio of the polycarboxylic acid to polyol in polymerization is usually from 1/0.7 to 2/1, preferably from 1/0.9 to 1.2/1 in terms of equivalent ratio of carboxyl group/hydroxyl group. The acid value after the polycondensation is usually 100 or less, preferably 10 or less.

Specific Examples of Polyamide Resin

Suitable polyamide resins, the composition of which is not particularly restricted, include polycondensates of a polycarboxylic acid having 2 or more carboxyl groups with a polyamine having 2 or more amino groups, polycondensates of a compound having a carboxyl group and an amino group in the same molecule or anhydride thereof, and the like, Specific examples of the polycarboxylic acid having 2 or more carboxyl groups include the same ones as described in the column of the polyester resin.

Illustrative of the polyamine having 2 or more amino groups are hydrocarbon-based polyamines having 2 to 30 carbon atoms and 2 to 5 functional groups such as 4,4'-diaminodicyclohexylmethane; hexamethylenediamine, 1,5-pentanediamine, piperazine, 2,2,4-trimethylhexamethylenediamine and 2-ethyl-pentanediamine. The polyamines may be used alone or in admixture of two or more.

Illustrative of the compound having a carboxyl group-and an amino group in the same molecule or cyclized compound thereof include amino acids having 2 to 30 carbon atoms such as ε-aminoundecanoic acid, lactams having 4 to 10 carbon atoms such as lauryllactam, enantholactam and ε-caprolactam.

The polyamide resin, constituent component of,the treating agent of the present invention can be obtained by a conventional method, for example, by polycondensing a polycarboxylic acid and a polyamine as mentioned above under dehydration. Further, the polyamide resin can also be obtained by polycondensation of a lower mono-hydric alcohol ester of a polycarboxylic acid, for example, a de-methanol reaction of a polymethyl ester thereof with a polyamine. Further, the polyamide resin can be obtained also by ring-opening polymerization of a cyclized material. The polycondensation temperature is usually from 120 to 300° C., preferably from 150 to 220° C. The polymerization is desirably conducted in an atmosphere in the presence of an inert gas such as nitrogen and the like. The equivalent ratio of the polycarboxylic acids to polyamines in polymerization is usually from 1/0.7 to 2/1, preferably from 1/0.9 to 1.2/1 in terms of equivalent ratio of amine group/hydroxyl group. The amine value after the polycondensation is usually 100 or less, preferably 10 or less.

The molecular weight of the vinyl resin, polyester resin and polyamide resin obtained as described above is not particularly restricted. In the case of a non-cross-linked type resin, the resin has a weigh-average molecular weight of usually from 5000 to 2000000, preferably from 10000 to 500000, particularly preferably from 20000 to 300000. In the case of a cross-linked type resin, the resin has a molecular weight between crosslinking points of usually from 2000 to 100000, preferably from 5000 to 50000.

Specific Example of Silicone Resin

As the silicone resin, there may be listed dimethyl silicone resins or organo-modified silicone resins thereof. Organo-modified silicone resins are preferable. Specifically, there can be mentioned, for example, amino-modified silicone resins having a primary, secondary or tertiary amino group at a side chain or end and having a molecular weight per one amino group of 600 to 8000, carboxyl-modified silicone resins having a carboxyl group at a side chain or end and having a molecular weight per one carboxyl group of 750 to 3500, amide-modified silicone resins obtainable by further modifying an amino-modified silicone resin as mentioned above with an aliphatic or aromatic monocarboxylic acid group-containing compound having 1 to 30 carbon atoms, polyether-modified silicone resins containing a polyether group(s) (composed of aliphatic oxide having 2 to 5 carbon atoms; and having a polymerization degree of from 2 to 100) at a side chain or both ends in an amount of from 5 to 80 wt % based on the total weight, as well as other resins.

The above-described silicone resin can be produced, for example, by the following method. A dimethyl silicone resin is obtained by polymerizing a dimethyldichlorosilane monomer as a starting raw material. The organo-modified silicone resin is obtained by adding an allyl compound such as allyl amine, allyl alcohol, allyl chloride or the like to a silicone resin having a hydrosilane group (—Si—H) at a side chain or end at room temperature using a platinum catalyst, and if necessary, by further reacting an aliphatic oxide or the like with the adduct. The molecular weight of the above-mentioned silicone resin is not particularly restricted, and in general from 5000 to 2000000, preferably from 10000 to 500000 in terms of weight-average molecular weight.

Specific Examples of Cationic Urethane Resin

Cationic rethane resins include polyurethanes and/or polyureas derived from an active hydrogen-containing compound (A) and a polyisocyanate compound (B), at least a part of (A) comprising (a) an active hydrogen-containing compound having a tertiary amino (salt) group and/or (b) an active hydrogen-containing compound having a quaternary ammonium salt.

As active hydrogen-containing group in the active hydrogen-containing compound (a) having a tertiary amino (salt) group, there can be listed a hydroxyl group, mercapto group and amino group.

Compounds having a tertiary amino group and an active hydrogen-containing group are not particularly restricted, and include (a1) compounds represented by the following general formula (1), (a2) alkylene oxide adducts thereof, and (a3) polyester diols, polyamide diamines and polythioester dimercaptanes obtainable by condensing a dicarboxylic acid with each of the above-described compounds.

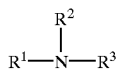

General formula

In the formula, $R^1$, $R^2$ and $R^3$ represent a hydrocarbon group, hydroxyalkyl group, mercaptoalkyl group, carboxylalkyl group or aminoalkyl group having 1 to 24 carbon atoms, and at least one of $R^1$, $R^2$ and $R^3$ is a hydroxyalkyl group, mercaptoalkyl group or aminoalkyl group.

Specific examples of compounds (a1-1) having a tertiary amino group and a hydroxyl group include N,N-diethylethanolamine, N,N-dibutylethanolamine, N,N-dimethylethanolamine, N-methyl-diethanolamine, N-ethyldiethanolamine, N-methyldipropanolamine, N-lauryldiethanolamine, N-methyl-N-hydroxyethylaniline, N-ethyl-N-hydroxyethylaniline, N,N-dioxyethylaniline, N,N-dioxyethyltoluidine, N-cyclohexyldiethanolamine, triethanolamine and the like.

Specific examples of compounds (a1-2) having a tertiary amino group and an amino group include N,N-dimethylhydrazine, N,N-dimethylethylenediamine, bis-(aminopropyl)-methylamine, bis-(aminoethyl)-methylamine, bis-(aminomethyl)-methylamine, bis-(aminoethyl)-ethylamine, bis-(aminoethyl)-cyclohexylamine, N-methyl-N-aminoethyltoluidine, bis-aminopropylalinine and the like.

Specific examples of compounds (a1-3) having a tertiary amino group and a mercapto group include N,N,N-diethylmercaptoethylamine, N,N,N-dibutylmercaptoethylamine, N,N,N-dimethylmercaptoethyl-amine, N,N,N-dimercaptoethylmethylamine, N,N,N-dimercaptoethyl-methylamine, N,N,N-dimercaptopropylmethylamine, N,N,N-dimercaptoethylstearylamine, N-methyl-N-mercaptoethylalinine, N,N-dimercaptoethylaniline, N,N-dimercaptoethyltoluidine, N,N,N-dimercaptoethylcyclohexylamine and the like.

Specific examples of compounds (a1-4) containing a tertiary amino group and having a hydroxyl group and an amino group include N-methyl-N-(aminoethyl)ethanolamine, N-ethyl-N-(aminopropyl)-ethanolamine, N-hydroxyethyl-N-aminoethylaniline and the like.

Specific examples of compounds (a1-5) containing a tertiary amino group and having a hydroxyl group and a mercapto group include N-methyl-N-(mercaptoethyl)ethanolamine, N-ethyl-N-(mercaptoethyl)ethanolamine, N-methyl-N-(mercaptomethyl)-ethanolamine, N-methyl-N-(mercaptopropyl)ethanolamine, N-methyl-N-(mercaptoethyl)propanolamine and the like.

Specific examples of compounds (a1-6) containing a tertiary amino group and having an amino group and a mercapto group include N-methyl-N-(aminoethyl)mercaptoethylamine, N-methyl-N-(aminobutyl)mercaptoethylamine, N-methyl-N-(aminoethyl)-mercaptolaurylamine, N-methyl-N-(aminoethyl)mercaptostearyl-amine, N-methyl-N-(aminobutyl)mercaptoethylamine and the like.

In the alkylene oxide adducts (a2) of the compound (a1) represented by the general formula (1), alkylene oxides include, for example, ethylene oxide (EO), propylene oxide (PO), 1,2-, 2,3- or 1,3-butylene oxide, tetrahydrofuran (THF) and epichlorohydrine. The alkylene oxide may be used alone or in combination of two or more, and in the latter case, block addition or random addition or mixed system thereof may be utilized.

The polyester diols, polyamide diamines and polythioester dimercaptanes (a3), obtainable by condensing a dicarboxylic acid with a compound (a1) represented by the general formula (1) or its alkylene oxide adducts (a2), are ones having at least two active hydrogen-containing groups obtainable by condensing a dicarboxylic acid with one having 2 or 3 active hydrogens among the compounds (a1) or adducts (a2). Examples of the dicarboxylic acid include aliphatic dicarboxylic acids (succinic acid, adipic acid, azelaic acid, sebacic, acid and the like), aromatic dicarboxylic acids (terephthalic acid, isophthalic acid, phthalic acid and the like), and mixture of two or more of them.

Beside the above-described compounds, there can also be used any compounds as described in Japanese Patent Publication (JP-B) No. 43-9076, as far as having an active hydrogen-containing group and a tertiary amino group.

Of these compounds (a) containing a tertiary amino group and having an active hydrogen-containing group, preferable are compounds containing a tertiary amino group and having a hydroxyl group, and further preferable is N-methyldiethanolamine.

As the active hydrogen-containing compound (a) having a tertiary amino (salt) group, those obtainable by neutralizing a compound (a1), (a2) or (a3) as described above with an inorganic acid, organic acid or mixture of two or more of them can be listed.

As specific examples of the inorganic acid and organic acid, there can be used the same ones as described in the method described afterward for introducing a cationic group into a resin skeleton.

Active hydrogen-containing compounds (b) having a quaternary ammonium salt group are not particularly restricted, and include ones represented by the general formula (2), specifically, ① quaternates and ② ampholytizates of the above-described tertiary amino (salt) group-containing active hydrogen-containing compound (a). Quaternization or ampholytization (modification) of the tertiary amino (salt) group-containing active hydrogen-containing compound, may be done through a method previously conducting the modification before polymerization, or a method conducting the modification after polymerization. Preferable is the method conducting the modification after polymerization.

In the formula, $R^1$, $R^2$ and $R^3$ are the same as defined above, $R^4$ represents a hydrocarbon group or carboxyalkyl group having 1 to 24 carbon atoms and X represents a halogen atom, monoalkyl carbonate or monoalkyl sulfate.

Compounds used for quaternizing a tertiary amino group are not particularly restricted, and include usually aliphatic monohalogenated alkyls, aromatic monohalogenated alkyls, dialkyl carbonates, dialkyl sulfates and the like.

The content of a tertiary amino (salt) group and/or quaternary ammonium salt group in the cationic urethane resin is usually from 0.01 to 3 m eq/g, preferably from 0.02 to 2.5 m eq/g per polyurethane or polyurea from the standpoints of water-resistance of a film and affinity to hair.

The active hydrogen-containing compound (A) other than the above-described compound (a) or (b) is not particularly restricted, and there can be listed high molecular weight polyols, polyamines, low molecular weight active hydrogen-containing compounds and the like.

High molecular weight polyols include, for example, polyether polyols, polyester polyols and silicone polyols.

Polyether polyols include compounds having a structure in which an alkylene oxide has been added to a polyfunctional active hydrogen-containing compound, and mixtures of two or more of these compounds.

As this active hydrogen-containing polyfunctional compound, there may be mentioned polyhydric alcohols, polyhydric phenols, amines, polycarboxylic acids and the like.

Specific examples of polyhydric alcohols include dihydric alcohols such as ethylene glycol, propylene glycol, 1,3-butylene glycol, 1,4-butanediol, 1,6-hexanediol, diethylene glycol, neopentyl glycol, bis(hydroxymethyl)cyclohexane and bis(hydroxyethyl)benzene; tri- to octa- polyhydric alcohols such as glycerine, trimethylolpropane, pentaerythritol, diglycerine, sorbitol, mannitol, dipentaerythritol, glucose, fructose and sucrose.

Specific examples of polyhydric phenols include polyhydric phenols such as pyrogallol, catechol and hydroquinone, as well as, bisphenols, such as bisphenol A, bisphenol F and bisphenol S.

Specific examples of amines include monoamines, for example, ammonia, alkylamines containing 1 to 20 carbon atoms (such as butylamine) and aniline; aliphatic polyamines, such as ethylenediamine, trimethylenediamine, hexamethylenediamine and diethylenetriamine; heterocyclic polyamines, for instance, piperazine, N-aminoethylpiperazine and other ones as described in JP-B No. 55-21044; alicyclic polyamines, such as dicyclohexylmethanediamine and isophoronediamine; aromatic polyamines, such as phenylenediamine, tolylenediamine, xylylenediamine, diphenylmethanediamine, diphenyl ether diamine and polyphenylmethane-polyamine; and alkanol amines, such as monoethanolamine, diethanolamine, triethanolamine and triisopropanolamine; and the like.

Specific examples of polycarboxylic acids include aliphatic polycarboxylic acids such succinic acid and adipic acid and aromatic polycarboxylic acids such as phthalic acid, terephthalic acid and trimellitic acid.

The above-described active hydrogen-containing polyfunctional compounds can also be used in combination of two or more.

Alkylene oxides to be added to the active hydrogen-containing polyfunctional compound include the same ones as described above.

The alkylene oxides may be used alone or in combination of two or more, and in the latter case, block addition (such as tipped, balanced and activated secondary types) or random addition or mixed system of them may be used.

Of them, preferable are EO alone, PO alone, THF alone, combinations of EO with PO, and THF with PO and/or EO (in the case of combination, random, block and mixed system thereof), and THF alone is particularly preferable.

Addition of an alkylene oxide to an active hydrogen-containing polyfunctional compound can be conducted by a usual method, in a single stage or multi stages, at normal pressure or under pressure; in the absence or presence of a catalyst (alkali catalyst, amine-based catalyst, acidic catalyst). Particularly in the last stage of alkylene oxide addition, it is preferably conducted in the presence of a catalyst.

Further, polyether polyols may be ones of increased molecular weight through reaction with a small amount of a polyisocyanate described below (equivalent ratio of polyalkylene ether polyol/polyisocyanate: for example, usually from 1.2 to 10/1, preferably from 1.5 to 2/1).

Polyether polyols have an equivalent weight (molecular weight per hydroxyl group) of usually from 100 to 10000, preferably from 250 to 5000, further preferably from 500 to 1500. Further, polyether polyols have a functionality of usually from 2 to 8, preferably from 2 to 3, particularly preferably 2.

Among these polyether polyols, preferred are alkylene oxide adducts of a polyhydric alcohol, and particularly polypropylene glycols and polytetramethylene glycols.

Polyester polyols include, for example, condensed polyester diols obtainable by reacting a low molecular weight-diol and/or polyether diol with a dicarboxylic acid, polylactonediols obtainable by ring-opening polymerization of a lactone, and polycarbonate diols obtainable by reacting a low molecular weight diol with a carbonate diester of a lower alcohol (such as methanol).

Low molecular weight diols in the above include ethylene glycol, diethylene glycol, propylene glycol, dipropylene glycol, 1,4- and 1,3-butane diols, neopentyl glycol, 1,6-hexane diol; cyclic group-containing low molecular weight diols [for example, those described in JP-B No. 45-1474; such as bis(hydroxymethyl)-cyclohexane, bis(hydroxyethyl) benzene and bisphenol A ethylene oxide adduct].

Polyether diols include bifunctional ones among of- polyether polyols as described above.

Dicarboxylic acids include aliphatic dicarboxylic acids (succinic acid, adipic acid, azelaic acid, sebacic acid and the like), aromatic dicarboxylic acids (terephthalic acid, isophthalic acid, phthalic acid and the like), and mixture of two or more of them; and lactones include ε-caprolactone, γ-butyrolactone, γ-valerolactone and mixtures of two or more of them.

Polyesters can be produced by a usual method, for example, by reacting (condensing) a low molecular weight diol and/or a polyether diol with a dicarboxylic acid or an ester-forming derivative thereof [for example, anhydrides (maleic anhydride, phthalic anhydride and the like), lower esters (methyl adipate, dimethyl terephthalate and the like), halides and the like] or with an anhydride thereof and an alkylene oxide (for example, ethylene oxide and/or propylene oxide), or by adding a lactone to an initiator (low molecular weight diol and/or polyether diol).

Illustrative of these polyester polyols are polyethylene adipate diol, polybutylene adipate diol, polyhexamethylene adipate diol, polyneopentyl adipate diol, polyethylene/propylene adipate diol, polyethylene/butylene adipate diol, polybutylene/hexamethylene adipate diol, polydiethyene adipate diol, poly(polytetramethylene ether) adipate diol, polyethylene azelate diol, polyethylene sebacate diol, polybutylene azelate diol, polybutylene sebacate diol, polycaprolactone diol or triol, polyhexamethylene carbonate diol and the like.

Silicone polyols are not particularly restricted, and include those represented by the following general formula (3).

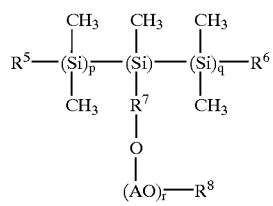

(3)

In the formula, each of $R^5$, $R^6$ and $R^8$ represents a hydrogen atom, hydroxyl group, a straight-chain or branched alkyl group containing 1 to 24 carbon atoms, $R^7$ represents a straight-chain or branched alkylene group containing 1 to 24 carbon atoms, A represents a straight-chain or branched alkylene group having 2 to 10 carbon atoms, and each of p, q and r represents an integer of 1 to 100.

Polyamines among active hydrogen-containing compounds (A) include, for example, aliphatic polyamines (specifically, ethylenediamine, diethylenetriamine, hexamethylenediamine and the like), aromatic polyamines (phenylenediamines, diaminotoluenes, xylenediamines, mesithylenediamine, diphenyl ether and the like), alicyclic polyamies (isophoronediamine and other alicyclic polyamines and the like) and heterocyclic polyamines (piperazine and other heterocyclic polyamines described in JP-B No. 55-21044, and the like). Of these polyamines, aliphatic polyamines are preferable.

Low molecular weight active hydrogen-containing compounds include ones usually called a cross-linker or chain extender, having 2 or more, preferably from 2 to 5 active hydrogens in one molecule and having an active hydrogen equivalent of less than 200. Specific examples thereof include di or trihydric alcohols (ethylene glycol, propylene glycol, 1,3-butylene glycol, 1,4-butane diol, 1,6-hexane diol, glycerine, trimethylolpropane and the like), amines (diethanolamine, triethanolamine, triisopropanolamine, ethylenediamine, diethylenetriamine, isophoronediamine, diaminotoluene, diethyltoluenediamine, methylenedianiline, methylenebisorthochloroaniline and the like). Further, there may be also listed polyhydroxy compounds having an equivalent of less than 200 obtainable by adding a small amount of an alkylene oxide such as ethylene oxide and/or propylene oxide to a di or trihydric alcohol as mentioned above, a tetra to octahydric alcohol (pentaerythritol, methylglucoside, sorbitol, saccharose and the like), a polyhydric phenol (bisphenol A, hydroquinone or the like), an amines as mentioned above, an other amine (aminoethylpiperazine or aniline) or the like; as well as water. Of them, preferable are glycols, diamines and water.

Further, low molecular weight active hydrogen-containing compounds include ones usually called a terminator, for example, monoalcohols (hydroxyethyl acrylate, hydroxypropyl acrylate, hydroxyethyl methacrylate, hydroxypropyl methacrylate, trimethylolpropane diallyl ether and the like); and amines (butylamine, diallyl amine and the like). Of them, preferable are hydroxyethyl acrylate and hydroxypropyl acrylate.

The above-mentioned active hydrogen-containing compounds may be used alone or in admixture of two or more.

As the polyisocyanate compound (B), those conventionally used in polyurethane production can be used. Such polyisocyanate compounds are not particularly restricted, and include aromatic polyisocyanates containing 6–20 carbon atoms [for example, 1,3- and/or 1,4-phenyl diisocyanate, 2,4- and/or 2,6-tolylene diisocyanate (TDI), crude TDI, 2,4'- and/or 4,4'-diphenylmethane diisocyanate (MDI), crude MDI, naphthylene-1,5-diisocyanate and triphenylmethane-4,4',4"-triisocyanate]; aliphatic polyisocyanates containing 2 to 18 carbon atoms (for example, hexamehylene diisocyanate and lysine diisocyanate); alicyclic polyisocyanates containing 4 to 15 carbon atoms (for example, isophorone diisocyanate and dicyclohexylmethane diisocyanate); araliphatic polyisocyanates containing 8 to 15 carbon atoms (for example, xylene diisocyanate); and modified compounds of these isocyanates (modified ones containing urethane group, carbodiimide group, allophanate group, urea group, biuret group, urethodione group, uretoneimine group, isocyanurate group, oxzazolidon group or the like); and mixtures of two or more of them.

In producing the cationic urethane resin, constituent component of the present invention, the proportion of the active hydrogen—containing compound (A) to the polyisocyanate compound (B) can be variously changed, and the equivalent ratio of an isocyanate group to an active hydrogen is usually (from 0.5 to 2):1, preferably (1.05 to 1.5):1.

Production of the urethane resin can be conducted according to a known polyurethane production method. For example, there can be listed a method (prepolymer method) comprising reacting compounds (A) and (B) dividedly in multi stages, a method (one shot method) comprising reacting compounds (A) and (B) at one time and the like, and the prepolymer method is preferable. As the prepolymer method, there is exemplified a method which comprises reacting compounds (A) and (B) previously, and completing the reaction with a low molecular weight diamine or the like, followed by neutralizing and quaternizing the tertiary amine group partially or completely.

The above-mentioned reaction can be conducted in a solvent, which is desirably inert to isocyanate group. Suitable solvents include amide solvents (N-methylpyrrolidone, dimethylformamide, dimethylacetamide and the like); ketone solvent (acetone, methyl ethyl ketone, methyl isobutyl ketone, cyclohexanone and the like); aromatic hydrocarbon solvents (toluene, xylene and the like); etheric solvents (dioxane, tetrahydrofuran and the like); sulfoxide solvents (dimethylsulfoxide and the like), and mixed solvents of two or more of them. The amount of the solvent is usually from 0 to 400% based on the amount of the urethane resin. The reaction temperature is usually in mild range, for example, from 20 to 150° C., preferably from 20 to 100° C. Further, the reaction time is usually from 3 to 20 hours. The reaction pressure is usually at normal pressure, and may also be under pressure. Further, for accelerating the reaction, there may also be used a catalyst usually used, for example, an amine-based catalyst (triethylenediamine, N-methylmorpholine, triethylamine or the like), a tin-based catalyst (dibutyltindilaurate or the like), a lead-based catalyst (lead octylate or the like) or the like.

Specifier Examples of Ampholytic Urethane Resin

Ampholytic urethane resins include, for example, ones obtainable by modifying with an ampholytizing agent (such as sodium monochloroacetate), a copolymer of an organic diisocyanate (such as hexamethylene diisocyanate) and diol components comprising a polyether polyol (such as polytetramethylene glycol) and a diol containing a tertiary amine group (such as N-methyldiethanolamine). The ampholytic group introduction method and the urethane resin production method are the same as those described above excepting the cationic compounds. Specific examples of the ampholytic urethane resin include those described in Japanese Patent Lay-Open (JP-A) No. 10-259115.

The content of an ampholytic group in the ampholytic urethane resin is from 0.01 to 3 m eq/g, preferably from 0.02 to 2.5 m eq/g per an urethane resin or urea resin from the standpoints of water-resistance of a film and affinity to hair Specific Examples of Nonionic Urethane Resin Nonionic urethane resins include ones obtainable by copolymerizing an organic diisocyanate (such as hexamethylene diisocyanate) with a diol component comprising such a nonionic hydrophilic component as a polyether polyol (for example, polyethylene glycol) instead of an ionic group-containing diol. As the urethane resin production method, the same method as described above can be used excepting the ionic compounds. Specific examples of the nonionic urethane resin include a hexamethylene diisocyanate-polytetramethylene glycol copolymer, isophorone diisocyanate-polypropylene glycol copolymer and the like. The polyoxyethylene group content in a resin is usually from 20 to 95 wt %, preferably from 40 to 85 wt %.

The above-mentioned cationic, ampholytic or nonionic urethane resins are polyurethanes or polyureas, and can be made into a dispersion by a usual method (such method as described in JP-B No. 42-24192). For instance, an aqueous-dispersion (for example, concentration of about 45%) can be obtained by adding water under stirring to an acetone solution (for example, concentration of about 60%) of the resulting polyurethane or polyurea, followed by distilling off the acetone with heating.

The above-mentioned cationic, ampholytic and nonionic urethane resins have a molecular weight of 1000 or more, preferably from 5000 to 2000000, further preferably from 10000 to 1000000 in terms of weigh-average molecular weight. Of these urethane resins, preferable are cationic and ampholytic urethane resins, particularly cationic urethane resins.

Specific Examples of Cationic Group

In the present invention, cationic groups contained in the resin skeleton of the resin (T) are not particularly restricted, and include groups of primary, secondary or tertiary amine salts, quaternary ammonium salts, quaternary phosphonium salts and the like, and the quaternary ammonium salt group is preferable. The resin contains the cationic group in an amount of usually from 0.01 to 3 m eq/g, preferably from 0.03 to 0.25 m eq/g.

The introduction method of cationic group into the resin skeleton varies depending on the kind of the resin. The introduction method in the case of a cationic urethane resin is as described above, and as other examples, there may be listed (1) a method of using a cationic vinyl monomer as mentioned above in producing a vinyl resin, (2) a method of using a polyol containing a tertiary amino group as a part of the polyol component in producing a polyester resin, (3) a method of using a polyamine containing a tertiary amino group as a part of the polyamine component in producing a polyamide resin, (4) a method in which an amino group is introduced by utilizing a functional group at the side chain of a resin and, if necessary, quaternized, (5) a method in which a trialkyl (having 1 to 10 carbon atoms) phosphine is reacted to a resin containing a halogen to introduce a quaternary phosphonium salt, as well as other method.

Groups of primary, secondary and tertiary amine neutralizing salts include primary, secondary and tertiary amino groups neutralized with an organic acid, inorganic acid or mixture of two or more of them.

Inorganic acids include, for example, hydrochloric acid, sulfuric acid, phosphoric acid and nitric acid.

Organic acids are inclusive of carboxylic acids, sulfonic acids, monosulfates, phosphates and the like.

As the carboxylic acid, those having a carboxyl group in the molecule can be usually used, and compounds represented by the following general formula (4) or (5) are preferable.

$$R^9-COOH \tag{4}$$

$$R^{10}-O(A_2O)_1-CH_2-COOH \tag{5}$$

In the formulae, $R_9$ and $R^{10}$ represent hydrogen atoms, or straight-chain or branched hydrocarbon groups or hydroxyalkyl groups containing 1 to 24 carbon atoms, $A_2$ represents a straight-chain or branched alkylene group having 2 to 10 carbon atoms, and 1 represents an integer from 0 to 100.

Specific examples thereof include formic acid, acetic acid, propionic acid, lauric acid, stearic acid, behenic acid, isostearic acid, oleic acid, lactic acid, hydroxylauric acid, hydroxystearic acid, polyoxyethylene (polymerization degree is from 1 to 100) lauryl ether acetic acid, polyoxyethylene (polymerization degree is from 1 to 100) octyl ether acetic acid, polyoxyethylene (polymerization degree is from 1 to 100) stearyl ether acetic acid, polyoxypropylene (polymerization degree is from 1 to 100) lauryl ether acetic acid, polyoxypropylene (polymerization degree is from 1 to 100) octyl ether acetic acid, and the like.

As the sulfonic acid and monosulfate, there can usually be used those containing in the molecule a sulfonate group ormonosulfate ester group, and those represented by the general formula (6) are preferable.

$$R^{11}-(O)_mSO_3H \tag{6}$$

In the formula, $R^{11}$ represents a hydrogen atom, a straight-chain or branched aliphatic hydrocarbon group or hydroxyalkyl group containing 1 to 24 carbon atoms, or aromatic hydrocarbon group (for example, phenyl group, alkylphenyl group, naphthalene group and the like). m is a number of 0 or 1. Specific examples thereof include methyl sulfate, ethyl sulfate, isopropyl sulfate, propyl sulfate, octyl sulfate, lauryl sulfate, stearyl sulfate, isostearyl sulfate, methylsulfonic acid, ethylsulfonic acid, laurylsulfonic acid, stearylsulfonic acid, benzenesulfonic acid and alkylbenzenesulfonic acids.

As the phosphoric acid, those having in the molecule a phosphate ester group can be used, and those represented by the general formula (7) are preferable.

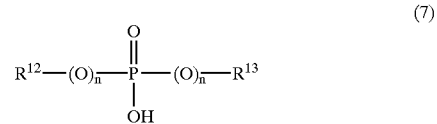

$$R^{12}-(O)_{\overline{n}}-\overset{\overset{\displaystyle O}{\|}}{\underset{\displaystyle OH}{P}}-(O)_{\overline{n}}-R^{13} \tag{7}$$

In the formula, each of $R^{12}$ and $R^{13}$ represents hydrogen atoms, straight-chain or branched hydrocarbon groups or hydroxyalkyl group having 1 to 24 carbon atoms. n is a number of 0 or 1.

Specific examples thereof include dimethyl phosphate, diethyl phosphate, methylethyl phosphate, methyl phosphite, diosopropyl phosphate, dilauryl phosphate, distearyl phosphate and the like.

As the inorganic acid and organic acid, any of those described in Keshohin Shubetsu Ninka Kijun 1994, Welfare Department, Yakumukyoku, Shinsaka, ed., 1994 (Yakuji Nippo sha) can be used, in addition to those exemplified above.

In the present invention, as the quaternary ammonium salt group, those obtainable by quaternizing tertiary amino groups can be listed. Methods for modifying a tertiary amino group (salt) include a method of conducting modification before polymerization, and a method of conducting modification after polymerization. Preferable is the id method of conducting modification after polymerization.

As the compound for quaternizing a tertiary amino group, the same ones as described in "specific example of cationic urethane resin" can be used.

The aliphatic monohalogenated alkyls are not particularly restricted, and include those represented by the general formula (8). Specific examples thereof include aliphatic monohalogenated alkyls having 1 to 30 carbon atoms, for example, methyl chloride, ethyl chloride, butyl bromide, methyl iodide, lauryl bromide, stearyl chloride, isopropyl iodide and the like. Of them, preferable are monohalogenated alkyls having 1 to 2 carbon atoms, particularly methyl chloride and ethyl chloride.

$$R^{14}-X \tag{8}$$

In the formula, $R^{14}$ represents a straight-chain or branched hydrocarbon group having 1 to 24 carbon atoms, X represents a halogen atom (Cl, Br, I and the like).

The aromatic monohalogenated alkyls are not particularly restricted, and specific examples thereof include aromatic monohalogenated alkyls having 7 to 15 carbon atoms such as benzyl chloride, benzyl bromide, benzyl iodide and the like, and benzyl chloride is preferable.

The dialkyl carbonates are not particularly restricted, and those represented by the general formula (9) are listed.

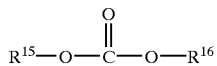

(9)

In the formula, each of $R^{15}$ and $R^{16}$ represents a straight-chain or branched hydrocarbon group having 1 to 24 carbon atoms.

Specific examples thereof include diethyl carbonate, dimethyl carbonate, dibutyl carbonate, diisoproply carbonate, dilauryl carbonate, distearyl carbonate and the like. Among them, dimethyl carbonate and diethyl carbonate are preferable.

The dialkyl sulfates are not particularly restricted, and those represented by the general formula (10) are listed.

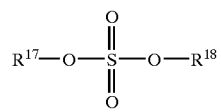

(10)

In the formula, each of $R^{17}$ and $R^{18}$ represents a straight-chain or branched hydrocarbon group having 1 to 24 carbon atoms.

Specific examples thereof include dimethyl sulfate, diethyl sulfate, dibutyl sulfate, diisopropyl sulfate, dilauryl sulfate, distearyl sulfate, dibehenyl sulfate and the like. Among them, dimethyl sulfate and diethyl sulfate are preferable.

Specific Examples of Ampholytic Group

In the present invention, the ampholytic group contained in the resin skeleton of the resin (T) is not particularly restricted, and those represented by each of following general formulae (11) to (14) are listed.

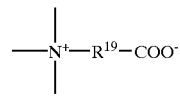

General formula (11)

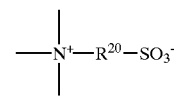

General formula (12)

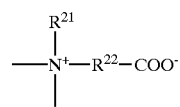

General formula (13)

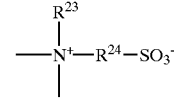

General formula (14)

In the formulae, $R^{19}$, $R^{20}$, $R^{22}$ and $R^{24}$ represent alkylene groups having 1 to 30 carbon atoms, and $R^{21}$ and $R^{23}$ represent hydrogen atoms or alkyl groups having 1 to 30 carbon atoms.

Examplary are betaine group in the case of the formula (11) (when $R^{11}$ is a methylene group), sulfobetaine group in the case of the formula (12), and amino acid groups having both of a carboxylic or sulfonic group and an amino group in the case of the formulae (13) and (14). Among them, betaine group is preferable. The resin contains an ampholytic group as mentioned above in an amount of usually from 0.01 to 3 m eq/g, preferably from 0.03 to 0.25 m eq/g.

The introduction method of ampholytic group into a resin skeleton varies depending on the kind of the resin. The introduction method in the case of an ampholytic urethane resin is as described above, and as other examples, there are listed (1) a method of using an ampholytic vinyl monomer as mentioned above in producing a vinyl resin, (2) a method of using a polyol containing a tertiary amino group as a part of the polyol component in producing a polyester resin and ampholytizing the amino group after polymerization, (3) a method of using a polyamine containing a tertiary amino group as a part of the polyamine component in producing a polyamide resin and ampholytizing the amino group after polymerization, as well as other in methods.

As the betaine group, those obtainable by betainizing a tertiary amino group can be listed. Compounds to betainize a tertiary amino group are not particularly restricted, and include, for example, monohalogenated acetic acids (chlorine, bromine, iodine and the like) or their salts. As the salts of amonohalogenated acetic acid, there can be usually used an alkali metal salt, alkaline earth metal salt, amine salt, or ammonium salt. Alkali metal salts include lithium salts, sodium salts, potassium salts and the like. Alkaline earth metal salts include magnesium salts, calcium salts and the like. Amine salts include amine salts containing 1 to 30 carbon atoms and having 1 to 6 functional groups, such as trimethylamine, triethylamine, triethanolamine, dimethylaminoethanol, aminomethylpropanol, pyridine, ethylenediamine and the like.

As the sulfobetaine group, those obtainable by sulfobetainizing a tertiary amino group are listed. Compounds to sulfobetainize a tertiary amino group is not particularly restricted, and include, for example, monohalogenated (chlorine, bromine, iodine and the like) alkyl (1 to 20 carbon atoms) sulfonic acids or their salts. As the salt of a monohalogenated alkylsulfonic acid, there may be usually used an alkali metal salt, alkali earth metal salt, amine salt or ammonium salt. Alkali metal salts and alkaline earth metal salts include the same ones as used for a betaine group.

As the amino acid type ampholitic group, those obtainable by carboxyalkylating a primary or secondary amino group may be listed. Compounds to carboxyalkylate a primary or secondary amino group are not particularly restricted, and include, for example, monohalogenated (chlorine, bromine, iodine and the like) alkyl (1 to 30 carbon atoms) carboxylic acids or their salts. As the salt of the monohalogenated alkyl carboxylic acid, there can be usually used an alkali metal salt, alkaline earth metal salt, amine salt or ammonium salt. Alkali metal salts and alkaline earth metal salts include those used for a betaine group.

Betainizing, sulfobetainizing and amino acid type ampholitization are usually conducted by reacting a compound containing a tertiary amino group and a monohalogenated acetic acid or its salt, or a monohalogenated alkyl carboxylic acid or salt thereof as described above, at 70 to 100° C. for 5 to 10 hours. The end point of the reaction can be judged by measuring the degree of quaternization.

Specific Examples of Anionic Group

In the present invention, the anionic group contained in the resin skeleton of the resin (T) is not particularly restricted, and there maybe listed a carboxyl group, sulfonic acid group, phosphoric group and the like. Among them, a carboxyl group and sulfonic acid group are preferable. The resin contains an anionic group in an amount of usually from 0.01 to 3 m eq/g, preferably from 0.03 to 0.25 m eq/g.

The introduction method of anionic group into a resin skeleton varies depending on the kind of the resin. For example, in the case of vinyl resin production, a method using an anionic monomer as mentioned above, and the like may be listed. In the case of a polyester resin and polyamide resin, there can be mentioned a method of conducting polymerization using an ester of a dicarboxylic acid having a sulfonic acid group introduced thereinto, a method of conducting sulfation, sulfonation, phosphation or the like using a hydroxyl group after polymerization, as well as other methods.

Specific Examples of Hydrophilic (Poly) oxyalkylene Group

In the present invention, the hydrophilic (poly) oxyalkylene group contained in the resin skeleton of the resin (T) is not particularly restricted, and usually a polyoxyethylene group, and there may be listed combination thereof with a polyoxypropylene group or hydroxyalkyl group. Of them, a polyoxyethylene group is preferable. The content of the polyoxyethylene group in a resin is usually from 20 to 95 wt %, preferably from 40 to 85 wt %.

The hydrophilic (poly)oxyalkylene group introduction method into a resin skeleton varies depending on the kind of the resin. For example, there can be listed (1) a method of using a nonionic monomer containing a (poly) oxyalkylene group as mentioned above in producing a vinyl resin, (2) a method of using a polyol containing a (poly)oxyalkylene group as a part of the polyol component in producing a polyester resin, (3) a method of using a polyamine containing a (poly)oxyalkylene group as a part of the polyamine component in producing a polyamide resin and ampholytizing the amino group after polymerization, as well as other methods.

Compounding Example of Urethane Resin

Further, in the present invention, physical properties can be controlled by compounding a urethane resin into at least one resin selected from the group consisting of a vinyl resin, polyester resin, silicone resin and polyamide resin. For example, the elongation and the like of the resulted resin film are further improved by compounding a urethane resin. Usable urethane resins are not particularly restricted, and include cationic, ampholytic and nonionic urethane resins as mentioned above, as well as anionic urethane resins.

Anionic urethane resins include ones obtainable by neutralizing with an acid (such as hydrochloric acid) a copolymer of an organic diisocyanate (such as hexamethylene diisocyanate) with a diol component comprising a polyether polyol (such as polytetramethylene glycol) and a carboxyl group-containing diol (such as dimethylolpropionic acid). Method of producing these urethane resins are the same as those described above excepting the cationic and ampholytic compounds. Specific examples of the anionic urethane resin include those described in JP-A No. 6-321741. Anionic group can be introduced, for example, by a method of using 2,2'-dihydroxymethyl-substituted carboxylic acid as one component of a diol to introduce a carboxyl group. The content of the anionic group in the anionic urethane resin is from 0.01 to 3 m eq/g, preferably from 0.02 to 2.5 m eq/g per polyurethane or polyurea from the standpoints of water-resistance of a film and affinity to hair. The anionic urethane resin can also be made into a dispersion similarly to the cationic urethane resin. The molecular weight of the anionic urethane resin is 1000 or more, preferably from 5000 to 2000000, further preferably from 10000 to 1000000 in terms of a weight-average molecular weight.

The compounding ratio of the above-mentioned vinyl resin, polyester resin, polyamide resin and silicone resin to the urethane resin is preferably from 2:98 to 95:5, preferably 10:90 to 10:1, particularly preferably 10:50 to 10:2 by weight. When the compounding ratio of the urethane resin is 5 or more or 98 or less, the elongation of the resulted film is excellent and setting property is further improved.

Physical Properties of Resin Film

In the present invention, a specimen of a resin film obtainable from the resin (T) has a 100% modulus of 8 to 40 kgf/cm as measured after being conditioned at 30 and of 80%R.H. (relative humidity), preferably 10 to 30 kgf/cm$^2$. When the 100% modulus at 30 and 80%R.H. is 8 kgf/cm$^2$ or more, it is possible to attain satisfactory setting ability, with little stickiness. On the other hand, when 40 kgf/cm$^2$ or less, set hair does not become hard, stiffness is not obtained, giving user natural feeling, and combing is improved.

The method for measuring the 100% modulus of a resin film is conducted under the following conditions.
(1) Production of Resin Film
(Film Having a Thickness of 0.2±0.05 mm)
As an example for producing the above film, there is a method described below.

A resin solution, which has been diluted and adjusted to a solid content of about 20% with water (if necessary, together with a lower boiling point organic solvent such as an alcohol, ketone or the like in part), is cast on to a horizontal release substrate (such as, polypropylene plate, and optionally, with a releasing agent or release paper) provided with a frame to give a thickness of 1 mm, and dried by leaving it at room temperature for about 12 hours. Then, it is dried for about 12 hours within an air circulating drier at about 60° C., and then released from the substrate to obtain a resin film having a thickness of 0.2±0.05 mm.
(2) Preparation of Measuring Specimen The above resin film is processed into a specimen using No. 3 dumbbell (JIS K6723), and the thickness is measured exactly, followed by moisture-conditioning the specimen within a thermo-hygrostat maintained at 30±2° C. and 80±5%R.H. Since the 100% modulus varies depending on humidified condition, a specimen humidified for 24 hours or more and 48 hours or less is used for measurement.
(3) Measurement Measurement is conducted using an autograph (for example, Autograph AGS-500D manufactured by Shimadzu Corp.) set within an atmosphere of a room temperature of 25±2° C. and a humidity of 65±5% R.H under the following conditions. The moisture-conditioned specimen taken out of the thermo-hygrostat is measured within 5 minutes.

1̂ Load cell: 5 kgf
2̂ Tensile speed: 50 mm/min.

In measuring lower 100% modulus of a thin resin film, the value varied depending on the tension speed, therefore, the measurement is conducted under the above conditions.

In the present invention, the loss tangent (tan δ) of a resin film is 0.3 or less, preferably 0.2. When tan δ is 0.3 or less, setting ability and recovery ability (recovering ability of set form from getting out of shapes) are excellent since the resin is of small viscosity.

The measurement of tan δ of a resin film is conducted under the following conditions.
(1) Production of Resin Film The production of a resin film is conducted by the method described for the above 100% modulus measurement.
(2) Production of a Measuring Specimen The above film is cut into a size of a length of 45 mm and a width of 5 mm using a cutter or the like to obtain a specimen, and the thickness of the specimen is measured exactly.
(3) Measurement Measurement is conducted using a commercially available viscoelasticity measuring apparatus (for example, MODEL DDV-25FP manufactured by ORIENTEC), under the following conditions to give tan δ at 25±1° C. as the measured value.

1̂ Load: 20 gf (variation: 0.3 to 3%)
2̂ Shaking frequency: 30 Hz

Production Method of Hair Treating Agent

The hair treating agent of the present invention comprises the above resin (T) and a diluent. The above resin (T) is insoluble in water. The hair treating agent is used in states of these resins having been dissolved with a diluent or dispersed in water. The diluent is a solvent and/or water, and used in states of liquid. dispersion (emulsion), water/solvent solution or water/solvent dispersion (emulsion), preferably is water dispersion (emulsion) or water/solvent dispersion (emulsion).The resin solid content in the hair treating agent is usually from 0.01 to 20 wt %, preferably from 0.1 to 10 wt %. As the solvent, an alcohol, ketone, ester, ether, hydrocarbon or the like having 1 to 10 carbon atoms can be used. Examples thereof include alcohols, such as methanol, ethanol, isopropanol, propylene glycol and dipropylene glycol, ketones, such as acetone, methyl ethyl keton and diethylketone, esters, such as methyl acetate, ethyl acetate and methyl propionate, ethers, such as methylcellosolve, ethylcellosolve and butyl cellosolve, hydrocarbons, such as petroleum ether, hexane and cyclohexane, and the like. Preferred are alcohols, particularly ethanol. The amount of a solvent in the hair treating agent varies depending on use thereof, and is usually from 0 to 90% based on the total amount.

Methods for producing the hair treating agent of the present invention are not particularly restricted, and include, for instance, a method in which a previously prepared resin is dissolved in a solvent or a mixed solvent of solvent/water, then, diluted with water or water/solvent mixed solvent, and dispersed or dissolved therein; and a method of conducting dispersion or dissolution simultaneously with polymerization to form a resin, such as emulsion polymerization, suspension polymerization and the like mentioned above, as well as other methods.

In the hair treating agent of the present invention, an anionic surfactant, nonionic surfactant, cationic surfactant or ampholytic surfactant may be used together in an amount which does not disturb the effect of the invention.

Anionic surfactants include, for example, sodium lauryl sulfate, sodium polyoxyethylene (polymerization degree=1 to 100) lauryl ether sulfate, triethanolamine salt of polyoxyethylene (polymerization degree=1 to 100) lauryl ether sulfate, sodium polyoxyethylene (polymerization degree=1 to 100) lauryl ether acetate, sodium polyoxyethylene (polymerization degree=1 to 100) palm oil fatty acid monoethanolamide suflate, disodium polyoxyethylene (polymerization degree=1 to 100) lauryl sulfosuccinate, disodium polyoxyethylene (polymerization degree=1 to 100) lauroylethanolamide sulfosucciante, palm oil fatty acid methyl taurine sodium salt, palm oil fatty-acid sarcosine sodium salt, palm oil fatty acid sarcosine triethanolamine salt, triethanolamine N-palm oil fatty acyl-L-glutamate, sodium N-palm oil fatty acyl-L-glutamate, lauroylmethyl-β-alanine sodium salt and sodium lauryl phosphate.

Nonionic surfactants include, for instance, 1:1 type palm oil fatty acid diethanolamide, lauryldimethylamine oxide, glycerine monostearate, ethylene glycol monostearate, polyethylene glycol (polymerization degree=1 to 100) monostearate, polyethylene glycol (polymerization degree=1 to 100) distearate, sorbitan monolaurate, polyoxyethylene (polymerization degree=1 to 100) sorbitan monolaurate, polyoxyethylene (polymerization degree=1 to 100) methylglucoside dioleate, polyoxyethylene (polymerization degree=1 to 100) tallow alkyl hydroxymyristylene ether and ethylene glycol monostearate.

Cationic surfactants include, for instance, stearyltrimethylammonium chloride, behenyltrimethylammonium chloride, distearyldimethylammonium chloride, lanorin fatty acid aminopropylethyldimethylammonium ethosul fate and lactate of stearic acid diethylaminoethylamide.

Ampholytic surfactants include, for example, palm oil fatty amidopropyldimethylaminoacetic acid betaine, lauryldimethylaminoacetic acid betaine, 2-alkyl-N-carboxymethyl-N-hydroxyethylimidazolinium betaine, laurylhydroxy sulfobetaine, sodium lauroylamidoethylhydroxyethylcarboxymethyl betaine hydroxypropyl phosphate and sodium β-laurylaminopropionate.

In the hair treating agent of the present invention, an additive, such as an emulsion stabilizer, humectant, silicone, chelating agent, thickening agent, perfume, colorant, preservative ultraviolet ray absorber or the like may be used together in an amount not disturbing the effects of the present invention.

Examples of emulsion stabilizer are higher alcohols having 6 to 22 carbon atoms such as cetyl alcohol, stearyl alcohol and behenyl alcohol. Illustrative of humectants are glycerol and sodium pyrrolidonecarboxylate. Exemplary of thickening agents are cationized cellulose, cationized guar gum, polyethylene glycol, sodium polyacrylate, hydroxyethyl cellulose and protein derivative. Examples of silicones include dimethylpolysiloxanes, modified silicones of a dimethylpolysiloxane, a part of methyl groups thereof having been substituted with an organic groups of various type, and cyclic dimethylsiloxanes. Chelating agents include, for example, sodium ethylenediamine tetraacetate and 1-hydroxyethane-1,1-diphosphonate.

Usage of Hair Treating Agent

The hair treating agent of the present invention, applications of which are not particularly restricted, is effective for fixatives such as mousse, mist and gel, shampoo, rinse, treatment, conditioning effect imparting agent, hair dye and the like. This hair treating agent can be applied to all uses of conventional hair treating agents having been used, utilizing excellent properties of the hair treating agent.

Using method of the hair treating agent can be depending on application thereof. For example, when used as a fixative such as mousse, mist and gel, the above hair treating agent is applied in a suitable amount on to hair, followed by arranging and drying the hair. When used as a shampoo, rinse or the like, it is applied to hair, and then washed with water or hot water. As described above, the hair treating agent has a resin solid content of usually from 0.01 to 20 wt %, preferably from 0.1 to 10 wt %.

When the hair treating agent of the present invention is used as a fixative such as mousse, mist or gel, if the resin content in the treating agent is less than 0.1 wt %, setting ability is deficient. On the other hand, if over 20 wt %, unnatural feeling is imparted to hair.

When it is used as a shampoo, if the resin content in the treating agent is less than 0.01 wt %, hair becomes straggling. On the other hand, if over 20 wt %, unnatural feeling is imparted after shampoo.

When it is used as a rinse, if the resin content in the treating agent is less than 0.01 wt %, hair becomes straggling. On the other hand, if over 20 wt %, unnatural feeling is imparted after shampoo.

When it is used as a treatment, if the resin content in the treating agent is less than 0.01 wt %, sufficient treatment effect is not obtained. On the other hand, if over 20 wt %, unnatural feeling is imparted after shampoo.

When it is used as a conditioning effect imparting agent, if the resin content in the treating agent is less than 0.01 wt %, sufficient conditioning effect is not obtained. On the other hand, if over 20 wt %, unnatural feeling is imparted to hair.

When it is used as a hair dye, if the resin content in the treating agent is less than 0.01 wt %, sufficient hair dying effect is not obtained. On the other hand, if over 20 wt %, unnatural feeling is imparted to hair.

Test Method of Hair Treating Agent

The methods for testing the hair treating agent of the present invention are as follows.

<Setting Property>

A resin solution or resin emulsion is diluted with water/ethanol (50/50) to obtain a diluted sample having a concentration of 3 wt % in terms of solid content. Then, 0.5 g of this diluted sample was applied to 2 g of hair bundle having a length of 25 cm, and this bundle was wound around a rod having a diameter of 10 mm. After drying, the hair bundle was removed from the rod, and the length of curl ($l_0$) was immediately measured. The length of curl ($l_0$) is a distance from fixed end to the lowest point of a hair bundle (h) of which one end is fixed and another end is allowed to be cernuous as shown in FIG. 1. Then this was suspended in a thermo-hygrostat (30° C., 80% R.H.) for 3 hours, followed by measuring the length of curl ($l_1$). The method for measuring the length of curl is the same as described above. Setting property was calculated according to the following formula from the length of curl ($l_0$) directly after removal from the rod and the length of curl ($l_1$) after left for 3 hours, and evaluated by the following judging standards.

Setting property (%)=[$(25-l_1)/(25-l_0)$]×100

| Judging standard | |
|---|---|
| Setting property 80 to 100% | ⊚ |
| Setting property 50 to 79% | ○ |
| Setting property 30 to 49% | Δ |
| Setting property 0 to 29% | X |

The hair bundle wound around the rod and dried under the same conditions as in the above setting test was washed with a 1% solution of a commercially available shampoo, and then washed with water and dried. The remaining amount of a resin on the surface of the hair was observed though a microscope (VH-6110, manufactured by KEYENCE) at a magnification of 1000, and evaluated by the following judging standard.

| Judging standard | |
|---|---|
| No residual resin | ○ |
| A small amount of residual resin | Δ |
| A large amount of residual resin | X |

The diluted sample produced in the above <setting property>was subjected to practical use test as a fixative by 10 panelists selected randomly from the whole workers in Sanyo Chemical Industries, Ltd., and stiffness, stickiness, combing property were evaluated by the following judging standard through functional evaluation.

| Judging standard | | |
|---|---|---|
| Stiffness | | |
| 7 or more panelists | felt no stiffness | ○ |
| 3 to 6 panelists | felt no stiffness | Δ |
| 8 or more panelists | felt stiffness | X |

-continued

| Judging standard | | |
|---|---|---|
| Stickiness | | |
| 7 or more panelists | felt no stickiness | ○ |
| 3 to 6 panelists | felt no stickiness | Δ |
| 8 or more panelists | felt stickiness | X |
| Combing property | | |
| 7 or more panelists | felt excellent combing property | ○ |
| 3 to 6 panelists | felt excellent combing property | Δ |
| 8 or more panelists | felt poor combing property | X |

BEST MODE FOR CARRYING OUT THE INVENTION

The present invention will be illustrated further by examples, but the present invention is not limited to them. In the following examples, part and % are parts by weight and % by weight respectively. Examples 1 to 12 are examples using the hair treating agent as a fixative.

EXAMPLE 1

Into a reaction vessel equipped with a thermometer, dropping funnel, cooling tube, nitrogen introducing tube and stirrer were charged 83 parts of methyl methacrylate, 196 parts of isotridecyl methacrylate, 8 parts of dimethylaminoethyl methacrylate, 1 part of azobisisobutylonitrile and 500 parts of methyl ethyl ketone, and polymerized for 4 hours under reflux by heating at 80° C. under nitrogen flow. The solution was cooled to 50° C., then, 6 parts of dimethyl sulfate was dropped to this and the mixture was stirred for 3 hours. After the completion of the reaction, 800 parts of water was added under stirring, and methyl ethyl ketone was distilled off under reduced pressure, to obtain a resin emulsion (I) having a solid content of 30%.

EXAMPLE 2

Into a reaction vessel equipped with a thermometer, dropping funnel, cooling tube, nitrogen introducing tube and stirrer were charged 140 parts of styrene, 140 parts of isotridecyl methacrylate, 8 parts of dimethylaminoethyl methacrylate, 1 part of azobisisobutylonitrile and 500 parts of methyl ethyl ketone, and polymerized for 4 hours under reflux by heating at 8° C. under nitrogen flow. The solution was cooled to 50° C., then, 6 parts of dimethyl sulfate was dropped to this and the mixture was stirred for 3 hours. After the completion of the reaction, 800 parts of water was added under stirring, and methyl ethyl ketone was distilled off under reduced pressure, to obtain a resin (II) emulsion having a solid content of 30%.

EXAMPLE 3

Into a reaction vessel equipped with a stirrer were charged 316 parts of water, 0.8 parts of sodium lauryl sulfate, 2 parts of sodium bicarbonate, 2.8 parts of dodecylmercaptane, 208 parts of styrene, 178 parts of butadiene and 9.9 parts of dimethylaminoethyl methacrylate to obtain a monomer emulsion. And separately, into an autoclave equipped with a stirrer were charged 198 parts of water, 0.4 parts of tetra sodium ethylenediamine tetraacetate, 0.4 parts of sodium lauryl sulfate, and 0.8 parts of potassium persulfate, the mixture was heated at 80° C., and 10% of the above monomer emulsion was added dropwise to the autoclave, and reacted for 1 hour. Next, 3.2 parts of potassium persulfate and 79 parts of water were added, then, the remaining monomer emulsion was dropped to this over 4 hours at 80° C. After completion of the dropping, the mixture was further stirred for 4 hours at 80° C. to age the polymerization. After completion of the polymerization, steam distillation was conducted at 80° C. to remove unreacted monomers. After cooling, pH was concrolled with a 10% phosphoric acid aqueous solution to 7, to obtain a resin (III) emulsion having a solid content of 30%.

EXAMPLE 4

Into a reaction vessel equipped with a thermometer, dropping funnel, cooling tube, nitrogen introducing tube and stirrer were charged 111 parts of styrene, 171 parts of lauryl methacrylate, 12 parts of dimethylaminoethyl methacrylate quaternized with methyl chloride, 60 parts of ethylene glycol dimethacrylate and 700 parts of water, and polymerized for 7 hours under reflux by heating at 80° C. under nitrogen flow, to obtain a resin (IV) emulsion having a solid content of 30%.

EXAMPLE 5

Into a reaction vessel equipped with a thermometer, dropping funnel, cooling tube, nitrogen introducing tube and stirrer were charged 254 parts of polytetramethylene glycol having a molecular weight of 3000, 25 parts of adipic acid and 10 parts of N-methyldiethanolamine, and polymerized for 10 hours at 150° C. under nitrogen flow to obtain a polyester resin having an acid value of 1.1 and a molecular weight of 30000. This resin was dissolved into 500 parts of dimethyl ketone, followed by controlling the temperature was to 50° C., dropping 11 parts of dimethyl sulfate thereto and stirring the mixture for 3 hours. After completion of the reaction, 800 parts of water was added under stirring, and then dimethyl ketone was distilled off under reduced pressure to obtain a resin (V) emulsion having a solid content of 30%.

EXAMPLE 6

Into a reaction vessel equipped with a thermometer, dropping funnel, cooling tube, nitrogen introducing tube and stirrer were charged 285 parts of a both end terephthalated compound of a polypropylene glycol having a molecular weight of 3000, 5 parts of ethylenediamine and 3 parts of diethylenetriamine, and polymerized for 10 hours at 180° C. under nitrogen flow to obtain a polyamide resin having an amine value of 2.0 and a molecular weight of 25000. This resin was dissolved into 500 parts of dimethyl ketone, followed by controlling the temperature to 50° C., dropping 7 parts of diethyl sulfate thereto and stirring the mixture for 3 hours. After completion of the reaction, 800 parts of water was added under stirring, dimethyl ketone was distilled off under reduced pressure to obtain a resin (VI) emulsion having a solid content of 30%.

PRODUCTION EXAMPLE 1 OF COMPOUNDING URETHANE RESIN

Into a sealed reaction vessel equipped with a thermometer and stirrer were charged 256.2 parts of a polytetramethylene glycol having a molecular weight of 2000, 0.7 parts of N-methyl-diethanolamine, 42.2 parts of isophorone diisocyanate and 122 parts of acetone, and the reaction system was purged with a nitrogen gas, then, reacted for 5 hours at 80° C. under stirring. To the resulted acetone solution was added 0.3 parts of methyl chloride and quaternized at 45 to 55° C.

The resulted quaternizate was cooled to 30° C., followed by adding 700 parts of water thereto and distilling off acetone at 50 to 60° C. under reduced pressure, to obtain 1000 parts of a resin (VII) emulsion having a solid content of 30%.

PRODUCTION EXAMPLE 2 OF COMPOUNDING URETHANE RESIN

Into a sealed reaction vessel equipped with a thermometer and stirrer were charged 90.7 parts of apolytetramethylene glycol having a molecular weight of 2000, 90.7 parts of a polyester diol composed of 3-methylpentanediol having a molecular weight of about 2000 and adipic acid, 6.6 parts of 1,4-butanediol, 15.0 parts of N-methyldiethanolamine, 83.3 parts of isophorone diisocyaante and 122 parts of acetone, and the reaction system was purged with a nitrogen gas, then, reacted for 5 hours at 80 under stirring. To the resulted acetone solution was added 14.7 parts of sodium monochloroacetate and ampholytized at 80° C. The resulted ampholytizate was cooled to 30° C., followed by adding 700 parts of water thereto and distilling off acetone at 50 to 60° C. under reduced pressure, to obtain 1000 parts of a resin (VIII) emulsion having a solid content of 30%.

EXAMPLE 7

100 parts of the resin (I) emulsion produced in Example 1 and 100 parts of the resin (VII) emulsion produced in Production Example 1 were mixed to obtain 200 parts of a resin (IX) emulsion having a solid content of 30%.

EXAMPLE 8

100 parts of the resin (I) emulsion produced in Example 1 and 900 parts of the resin (VIII) emulsion produced in Production Example 2 were mixed to obtain 1000 parts of a resin (X) emulsion having a solid content of 30%.

EXAMPLE 9

100 parts of the resin (V) emulsion produced in Example 5 and 500 parts of the resin (VII) emulsion produced in Production Example 1 were mixed to obtain 600 parts of a resin (XI) emulsion having a solid content of 30%.

EXAMPLE 10

100 parts of the resin (I) emulsion produced in Example 1 and 100 parts of the resin (VI) emulsion produced in Example 6 were mixed to obtain 200 parts of a resin (XII) emulsion having a solid content of 30%.

EXAMPLE 11

100 parts of the resin (II) emulsion produced in Example 2 and 200 parts of the resin (V) emulsion produced in Example 5 were mixed to obtain 300 parts of a resin (XIII) emulsion having a solid content of 30%.

EXAMPLE 12

485 parts of the resin (VIII) emulsion produced in Production Example 2 and 15 parts of the resin (III) emulsion produced in Example 3 were mixed to obtain 500 parts of a resin (XIV) emulsion having a solid content of 30%.

COMPARATIVE EXAMPLE 1

Into a reaction vessel equipped with a thermometer, dropping funnel, cooling tube, nitrogen introducing tube and stirrer were charged 180 parts of N-methacryloyloxyethyl N,N-dimethylammonium N-methylcarboxylate, 120 parts of stearyl methacrylate, 1.2 parts of azobisisoburylonitrile and 450 parts of anhydrous ethanol, and polymerized for 6 hours under reflux by heating at 80° C. under nitrogen flow. After the completion of the reaction, 250 parts of anhydrous ethanol was added to obtain a resin solution having a solid content of 30%.

COMPARATIVE EXAMPLE 2

Into a reaction vessel equipped with a thermometer, dropping funnel, cooling tube, nitrogen introducing tube and stirrer were charged 30 parts of styrene, 262 parts of 2-ethylhexyl acrylate, 8 parts of dimethylaminoethyl methacrylate, 1 part of azobisisobutylonitrile and 500 parts of methyl ethyl ketone, and polymerized for 4 hours under reflux by heating at 80° C. under nitrogen flow. The mixture was cooled to 50° C., followed by dropping 6 parts of dimethyl sulfate thereto and stirring the mixture for 3 hours. After the completion of the reaction, 800 parts of water was added under stirring, and methyl ethyl ketone was distilled off under reduced pressure, to obtain a resin emulsion having a solid content of 30%.

COMPARATIVE EXAMPLE 3

Into a reaction vessel equipped with a thermometer, dropping funnel, cooling tube, nitrogen introducing tube and stirrer were charged 196 parts of methyl methacrylate, 84 parts of stearyl methacrylate, 11 parts of dimethylaminoethyl methacrylate, 1 part of azobisisobutylonitrile and 500 parts of methyl ethyl ketone, and polymerized for 4hours under reflux by heating at 880 under nitrogen flow. The mixture was cooled to 50° c., followed by dropping 9 parts of sodium monochloroacetate thereto and stirring the mixture for 3 hours. After the completion of the reaction, 800 parts of water was added under stirring, and methyl ethyl ketone was distilled off under reduce pressure, to obtain a resin emulsion having a solid content of 30%.

COMPARATIVE EXAMPLE 4

Into a reaction vessel equipped with a thermometer, dropping funnel, cooling tube, nitrogen introducing tube and stirrer were charged 66 parts of methyl methacrylate, 220 parts of 2-ethylhexyl methacrylate, 8 parts of dimethylaminoethyl methacrylate, 1 part of azobsisobutylonitrile and 500 parts of methyl ethyl ketone, and polymerized for 4 hours under reflux by heating at 80° C. under nitrogen flow. The mixture was cooled to 50° C., followed by dropping 6 parts of dimethyl sulfate thereto and stirring the mixture for 3 hours. After the completion of the reaction, 800 parts of water was added under stirring, and methyl ethyl ketone was distilled off under reduced pressure, to obtain a resin emulsion having a solid content of 30%.

The evaluations of Examples 1 to 12 and Comparative Examples 4 are summarized in Table 1.

TABLE 1

| Number | Setting property | Washing property | Stiffness | Stickiness | Combing property | 100% modulus (kgf/cm$^2$) | tan δ |
|---|---|---|---|---|---|---|---|
| 1 | ◯ | ◯ | ◯ | ◯ | ◯ | 11 | 0.20 |
| 2 | ◯ | ◯ | ◯ | ◯ | ◯ | 28 | 0.08 |
| 3 | ◯ | ◯ | ◯ | ◯ | ◯ | 20 | 0.04 |
| 4 | ◯ | ◯ | ◯ | ◯ | ◯ | 27 | 0.02 |
| 5 | ◯ | ◯ | ◯ | ◯ | ◯ | 25 | 0.03 |

TABLE 1-continued

| Number | Setting property | Washing property | Stiffness | Stickiness | Combing property | 100% modulus (kgf/cm²) | tan δ |
|---|---|---|---|---|---|---|---|
| 6 | ○ | ○ | ○ | ○ | ○ | 23 | 0.05 |
| 7 | ◎ | ○ | ○ | ○ | ○ | 20 | 0.03 |
| 8 | ◎ | ○ | ○ | ○ | ○ | 24 | 0.01 |
| 9 | ◎ | ○ | ○ | ○ | ○ | 30 | 0.02 |
| 10 | ○ | ○ | ○ | ○ | ○ | 25 | 0.07 |
| 11 | ○ | ○ | ○ | ○ | ○ | 26 | 0.06 |
| 12 | ◎ | ○ | ○ | ○ | ○ | 15 | 0.01 |
| R1 | ○ | X | X | ○ | X | 60 | 0.04 |
| R2 | X | ○ | Δ | X | Δ | 3 | 0.90 |
| R3 | ○ | ○ | X | ○ | X | 70 | 0.08 |
| R4 | X | ○ | ○ | X | Δ | 15 | 0.72 |

Note: number in table represents number of example and comparative example, and R represents comparative example.

From the results shown in Table 1, it is known that the hair treating agents (Examples 1 to 12) of the present invention are excellent in washing property as compared with the conventional hair treating agent (Comparative Example 1). Further, Comparative Examples 2 to 4 are examples in which 100% modulus and tan δ are out of ranges of the present invention. When the 100% modulus is lower, setting property and stickiness deteriorate, and the 100% modulus is higher, stiffness and combing property become poor. Further, when tan δ is larger, setting property and stickiness become poor, leading to unsuitable use.

EXAMPLE 13

Example as Shampoo

| | % by weight |
|---|---|
| Sodium polyoxyethylene (n = 2) lauryl ether sulfate (25%) | 38 |
| Palm oil fatty acid amide propyl betaine liquid (30%) | 17 |
| Disodium sulfosuccinic acid polyoxyethylene (n = 5) lauroylethanolamide (30%) | 10 |
| Palm oil fatty acid diethanolamide | 3 |
| Resin (I) emulsion (30%) | 5 |
| Perfume, coloring agent and the like | Suitable amount |
| Water | Remaining amount |
| (Total) | 100 |

When the hair treating agent of the above blend was used as a hair shampoo, excellent foaming was manifested, integrated sense and feeling after drying were excellent, and excellent conditioning effect was observed.

EXAMPLE 14 (EXAMPLE AS HAIR RINSE)

| | % by weight |
|---|---|
| Distearyldimethylammonium chloride (90%) | 3 |
| Cetyl alcohol | 0.5 |
| Propylene glycol | 4 |
| Methylcellulose (#4000) | 1 |
| Resin (VI) emulsion (30%) | 3 |
| Perfume, coloring agent and the like | Suitable amount |
| Water | Remaining amount |
| (Total) | 100 |

When the hair treating agent of the above blend was used as a hair rinse, smooth feeling was obtained also during rinse, integrated sense and feeling after drying were excellent, and excellent conditioning effect was observed.

EXAMPLE 15 (EXAMPLE AS HAIR DYE)

| | % by weight |
|---|---|
| (First agent) | |
| p-Phenylenediamine | 3 |
| Resorcin | 0.5 |
| Oleic acid | 20 |
| Polyoxyethylene (n = 10) oleyl alcohol ether | 15 |
| Isopropyl alcohol | 10 |
| Aqueous ammonia solution (28%) | 10 |
| Resin (III) emulsion (30%) | 4 |
| Antioxidant, Chelating agent | Suitable amount |
| Water | Remaining amount |
| (Total) | 100 |
| (Second agent) | |
| Hydrogen peroxide (30%) | 20 |
| Stabilizer | Suitable amount |
| Water | Remaining amount |
| (Total) | 100 |

When the hair treating agent of the above blend was used as a hair dye, very smooth feeling was obtained, damage of hair was prevented, and excellent conditioning effect was observed.

The hair treating agent of the present invention has the following features and effects.

(1) When the hair treating agent of the present invention is applied to hair as a fixative, there are features that setting is not decomposed under higher temperature and high humidity, natural feeling does not disappear, washing removability from hair is excellent, and setting recovering ability and holding ability due to rubber elasticity of a resin film are excellent, and the like, as compared with conventionally used hair treating agents.

(2) When the hair treating agent of the present invention is applied to hair as a shampoo, rinse and hair dye, there are features that excellent conditioning effect is obtained, and the like.

INDUSTRIAL APPLICABILITY

Because of the above-described effects, the hair treating agent of the present invention is effective as a shampoo, rinse, treatment, conditioning effect imparting agent, hair dye and the like, in addition to as a fixative such as mousse, mist and gel, though the use thereof is not particularly restricted. Further, the hair treatment agent of the present invention can be applied to all of uses of conventionally used hair treatment agents, by utilizing the above-described excellent natures of the agent of the present invention.

What is claimed is:

1. A hair treating agent comprising:

a resin (T) and a diluent, the resin (T) providing a resin film having a tan δ of 0.3 or less and having a 100% modulus of 8 to 40 kgf/cm$^2$ as measured after having been conditioned at 30° C. and 80% relative humidity; the resin (T) being a compounded resin containing a urethane resin selected from the group consisting of a cationic urethane resin and an ampholytic urethane resin and at least one resin selected from the group consisting of a vinyl resin, a polyester resin, a polyamide resin and a silicone resin, in a weight ratio of said at least one resin to the urethane resin in the range of 2/98 to 95/5.

2. The hair treating agent of claim 1, wherein the cationic urethane resin comprises a polyurethane or polyurea derived from a polyisocyanate and an active hydrogen atom-containing compound, at least a part of the active hydrogen atom-containing compound being selected from the group consisting of an active hydrogen atom-containing compound (a) having a tertiary amino group or a salt thereof and an active hydrogen atom-containing compound (b) having a quaternary ammonium salt group.

3. The hair treating agent of claim 1, wherein the cationic urethane resin contains at least one cationic group selected from the group consisting of a tertiary amino group or a salt thereof and a quaternary ammonium salt group in an amount of 0.01 to 3 m eq/g.

4. A hair treating method which comprises treating hair with the hair treating agent of claim 1.

5. The hair treating agent of claim 1, wherein the urethane resin is a cationic urethane resin, having a weight-average molecular weight of at least 1,000.

* * * * *